(12) United States Patent
Wolinsky et al.

(10) Patent No.: US 6,764,446 B2
(45) Date of Patent: Jul. 20, 2004

(54) IMPLANTABLE PRESSURE SENSORS AND METHODS FOR MAKING AND USING THEM

(75) Inventors: Lone Wolinsky, Ramat Gan (IL); Eyal Doron, Kiriat-Yam (IL); Alon Ben-Yosefh, Haifa (IL); Avi Penner, Tel-Aviv (IL)

(73) Assignee: Remon Medical Technologies LTD (IL)

( * ) Notice: Subject to any disclaimer, the term of this patent is extended or adjusted under 35 U.S.C. 154(b) by 185 days.

(21) Appl. No.: 09/888,272

(22) Filed: Jun. 21, 2001

(65) Prior Publication Data

US 2002/0045921 A1 Apr. 18, 2002

Related U.S. Application Data

(63) Continuation-in-part of application No. 09/690,615, filed on Oct. 16, 2000, now Pat. No. 6,628,989.

(51) Int. Cl.[7] .................................................. A61B 5/04
(52) U.S. Cl. ........................................ 600/300; 607/61
(58) Field of Search ............................ 607/32, 33, 60, 607/61; 600/300, 301

(56) References Cited

U.S. PATENT DOCUMENTS

| | | | |
|---|---|---|---|
| 2,786,899 A | | 3/1957 | Carlisle |
| 3,672,352 A | | 6/1972 | Summers |
| 3,970,987 A | | 7/1976 | Kolm |
| 4,041,954 A | * | 8/1977 | Ohara .......................... 600/510 |
| 4,099,530 A | | 7/1978 | Chen et al. |
| 4,651,740 A | | 3/1987 | Schroeppel |
| 4,793,825 A | | 12/1988 | Benjamin et al. |
| 5,113,859 A | * | 5/1992 | Funke .......................... 607/30 |
| 5,749,909 A | * | 5/1998 | Schroeppel et al. .......... 607/61 |
| 5,833,603 A | * | 11/1998 | Kovacs et al. .............. 600/317 |
| 5,861,018 A | * | 1/1999 | Feierbach ..................... 607/60 |

(List continued on next page.)

FOREIGN PATENT DOCUMENTS

| | | |
|---|---|---|
| WO | WO 98/43338 | 10/1998 |
| WO | WO 99/34453 | 7/1999 |
| WO | WO 01/28627 A1 | 4/2001 |
| WO | WO 01/74278 A3 | 10/2001 |
| WO | WO 01/74278 A2 | 10/2001 |
| WO | WO 02/03347 A | 1/2002 |

OTHER PUBLICATIONS

American Heritage Dictionary Definition of "ultrasonic", 2000.*
Y. Porat, , et al., "Method for Transfer of Energy to an Electronic Circuit Implanted in a Living Body and a Device for Such Method", PCT Publication No. WO 98/43338, Oct. 1, 1998.
M. M. Friedman, "Piezoelectric Transducer", PCT Publication No. WO 99/34453, Jul. 8, 1999.
PCT Publication No. WO 00/47109 entitled Devices and Methods for Frequent Measurement of an Analyte Present in a Biological System.

*Primary Examiner*—George R. Evanisko
(74) *Attorney, Agent, or Firm*—Bingham McCutchen LLP

(57) ABSTRACT

An implant includes a pressure sensor, a controller for acquiring pressure data from the sensor, and an acoustic transducer for converting energy between electrical energy and acoustic energy. A capacitor is coupled to the acoustic transducer for storing electrical energy converted by the transducer and/or for providing electrical energy to operate the implant. The acoustic transducer may operate alternatively or simultaneously as an energy exchanger or an acoustic transmitter. During use, the implant is implanted within a patient's body, and an external transducer transmits a first acoustic signal into the patient's body, to energize the capacitor. The implant then obtains pressure data, and transmits a second acoustic signal to the external transducer, the second acoustic signal including the pressure data.

36 Claims, 6 Drawing Sheets

U.S. PATENT DOCUMENTS

| | | |
|---|---|---|
| 6,140,740 A | 10/2000 | Porat et al. |
| 6,164,284 A * | 12/2000 | Schulman et al. .......... 128/899 |
| 6,185,452 B1 * | 2/2001 | Schulman et al. ............ 607/60 |
| 6,200,265 B1 | 3/2001 | Walsh et al. |
| 6,236,889 B1 | 5/2001 | Soykan et al. |
| 6,248,080 B1 | 6/2001 | Miesel et al. |
| 2002/0045921 A1 | 4/2002 | Lone et al. |

* cited by examiner

IMPLANTABLE PRESSURE SENSORS AND METHODS FOR MAKING AND USING THEM

This application is a Continuation-in-Part of application Ser. No. 09/690,615, filed Oct. 16, 2000 now U.S. Pat. No. 6,628,989, the disclosure of which is expressly incorporated herein by reference.

FIELD OF THE INVENTION

The present invention relates generally to devices for implantation within a patient's body, particularly to pressure sensors that may be implanted within a body, and more particularly to implantable pressure sensors that may be energized, activated, controlled, and/or otherwise communicate via acoustic energy.

BACKGROUND OF THE INVENTION

Devices are known that may be implanted within a patient's body to monitor one or more physiological conditions and/or to provide therapeutic functions. For example, sensors or transducers may be located deep within the body for monitoring a variety of properties, such as temperature, pressure, strain, fluid flow, chemical properties, electrical properties, magnetic properties, and the like. In addition, devices may be implanted that perform one or more therapeutic functions, such as drug delivery, defibrillation, electrical stimulation, and the like.

Often it is desirable to control such devices once they are implanted within a patient by external command, for example, to obtain data, and/or to activate or otherwise control the implant. An implant may include wire leads from the implant to an exterior surface of the patient, thereby allowing an external controller or other device to be directly coupled to the implant. Alternatively, the implant may be remotely controlled, e.g., using an external induction device. For example, an external radio frequency (RF) transmitter may be used to communicate with the implant. RF energy, however, may only penetrate a few millimeters into a body, because of the body's dielectric nature. Thus, RF energy may not be able to communicate effectively with an implant that is located deep within the body. In addition, although an RF transmitter may be able to induce a current within an implant, the implant's receiving antenna, generally a low impedance coil, may generate a voltage that is too low to provide a reliable switching mechanism.

In a further alternative, electromagnetic energy may be used to control an implant, since a body generally does not attenuate magnetic fields. The presence of external magnetic fields encountered by the patient during normal activity, however, may expose the patient to the risk of false positives, i.e., accidental activation or deactivation of the implant. Furthermore, external electromagnetic systems may be cumbersome and may not be able to effectively transfer coded information to an implant.

Accordingly, a sensor, such as a pressure sensor, that may implanted within a patient's body, and may be energized by, controlled by, and/or otherwise communicate effectively with an external interface would be considered useful.

SUMMARY OF THE INVENTION

The present invention is generally directed to implants that may be implanted, e.g., using open surgical or minimally invasive techniques, or otherwise located within a mammalian body for monitoring pressure or other physiological parameters and/or for performing one or more therapeutic functions.

In accordance with a first aspect of the present invention, an implant is provided that includes a pressure sensor for measuring intra-body pressure. A controller is coupled to the pressure sensor for acquiring pressure data from the pressure sensor. One or more acoustic transducers are provided for converting energy between electrical energy and acoustic energy. Preferably, the one or more acoustic transducers are configured for converting acoustic energy from a source external to the implant into electrical energy and/or for transmitting an acoustic signal including the pressure data to a location external to the implant. One or more energy storage devices are coupled to at least one of the one or more acoustic transducers, the energy storage device(s) configured for storing electrical energy converted by the one or more acoustic transducers. The energy storage device(s) may be coupled to the controller for providing electrical energy to support operation of the implant. The energy storage device may include one or more capacitors, for example, a first relatively fast-charging capacitor and a second relatively slow-charging capacitor. In addition or alternatively, the energy storage device may include a rechargeable and/or nonrechargeable battery.

In a preferred embodiment, the one or more acoustic transducers may be a single transducer configured to operate alternatively as either an energy exchanger or an acoustic transmitter. Alternatively, the acoustic transducers may include an acoustic transmitter coupled to the controller for transmitting the acoustic signal to a location external to the body. In addition or alternatively, the acoustic transducers may include an energy exchanger coupled to the energy storage device, the energy exchanger including a piezoelectric layer for converting acoustic energy striking the piezoelectric layer into electrical energy.

The components of the implant may be attached to a substrate, such as a printed circuit board (PCB), and may be secured within a casing. The casing may include one or more openings through which active areas of the pressure sensor and/or the energy transducer may be exposed to a region exterior to the casing. Alternatively, the active area of the pressure sensor may be covered with a seal, such as silicone, Parylene C, or a relatively thin metal layer. In a further alternative, the casing may include a relatively thin foil or thin-walled region for sealing at least one of the pressure sensor and the energy transducer from a region exterior to the casing. The casing may be filled with a fluid, gel, and/or low modulus material, such as silicone, for coupling the pressure sensor and/or the energy transducer to the foil or thin-walled region. Thus, the thin-walled region may be used to couple the pressure sensor and/or energy transducer to a region exterior to the casing.

In accordance with another aspect of the present invention, a method is provided for making an energy exchanger for converting between acoustic and electrical energy. First, a layer of piezoelectric polymer is provided, such as a fluorocarbon polymer, preferably poly vinylidene fluoride (PVDF), or a copolymer of PVDF, such as PVDF-TrFE. The layer of polymer may be etched, e.g., to cleave carbon-fluorine, carbon-hydrogen, and/or carbon-carbon bonds, for example, using a sodium naphthalene solution (for carbon-fluorine bonds), or using a gas phase plasma treatment including oxygen, air, Argon, Helium, and/or other gas plasma (e.g., $SF_6$). A conductive layer may be applied onto the layer of polymer. The layer of polymer generally includes first and second surfaces, and first and second conductive layers are applied onto the first and second surfaces of the layer of polymer.

An adhesive, such as an epoxy or acrylic adhesive, is applied, e.g., atomized, over a substrate including one or more cavities therein. The piezoelectric layer is applied to a surface of the substrate. Pressure may be applied between the piezoelectric layer and the substrate, thereby causing the piezoelectric layer to become at least partially depressed within the one or more cavities. The adhesive may be cured, for example, using heat and/or pressure, and/or by exposure to visible or ultraviolet light.

The energy exchanger may then be incorporated into an implant, such as that described above. A substrate, e.g., a printed circuit board (PCB), e.g., made from FR4, Rogers, ceramic, Kapton, Teflon, PVDF, and/or PEEK, may be provided having an opening therethrough. A pressure sensor may be attached to the substrate adjacent the opening, the pressure sensor including an active area exposed via the opening for measuring intra-body pressure. A controller may be attached to the substrate and coupled to the pressure sensor for acquiring pressure data from the pressure sensor. An energy exchanger may be attached to the substrate, the energy exchanger coupled to the controller for at least one of converting acoustic energy from a source external to the implant into electrical energy and transmitting an acoustic signal, e.g., including the pressure data and optionally other information, to a location external to the implant. Finally, an energy storage device may be attached to the substrate and coupled to the energy exchanger, the energy storage device configured for storing electrical energy converted by the acoustic transducer and/or for providing electrical energy to support operation of the implant. The substrate and attached components may then be received in a casing for sealing the implant.

In accordance with yet another aspect of the present invention, a method is provided for acquiring data from an implant, such as that described above, that is implanted within a patient's body, using an external transducer located outside the patient's body. Generally, the external transducer transmits a first acoustic signal into the patient's body, the first acoustic signal being converted into electrical energy for operating the implant. The first acoustic signal may include an identification code (e.g., a serial number, model number, and/or other identifier) identifying a target implant, or other information, which may be interpreted by the implant. The implant may confirm that the identification code matches the implant, whereupon the implant may sample data and transmit a second acoustic signal to the external transducer.

In response, the external transducer receives the second acoustic signal from the implant, the acoustic signal including data related to a condition with the patient's body measured by the implant. Preferably, the external transducer automatically switches from an energizing mode after transmitting the first acoustic signal to a receiving mode for receiving the second acoustic signal. Upon completion of transmitting the data, e.g., after a power level of the implant falls below a predetermined level and/or after a predetermined time, the implant returns to a passive mode, awaiting further energizing or activation by the external transducer. Alternatively, after receiving the second acoustic signal, the external transducer may automatically switch back and forth from the energizing mode to the receiving mode, thereby alternately energizing the implant and receiving data from the implant. For example, the external transducer may transmit an energizing signal during any pause in operation of the implant, e.g., whenever the energy exchanger is available to receive the energizing signal. This may allow the external transducer to maintain the implant substantially fully charged, thereby allowing substantially indefinite operation. In a further alternative, the first and second acoustic signals may be transmitted simultaneously, e.g., at different frequencies.

In an alternative embodiment, the first acoustic signal transmitted by the external transducer may be a diagnostic signal, e.g., including a broad band signal or a scanning signal, that may be used to determine an optimal frequency for communicating with the implant. The implant may transmit at different frequencies in response to the diagnostic signal, and the external transducer may determine the optimal frequency for communicating with the implant. Alternatively, when the implant detects the diagnostic signal at an optimal frequency, it may respond with a second acoustic signal identifying or merely transmitting at the optimal frequency.

In yet another alternative embodiment, the energy storage device of the implant may include a relatively fast-charging device and a relatively slow-charging device. When the implant receives a first acoustic signal, it may immediately charge the fast-charging device, thereby allowing the implant to transmit a prompt response to the external transducer, e.g., within about fifty to two hundred milliseconds or less. The transmitted response may include an identification code, a confirmation that the implant is operational, and the like. While the implant is responding, the slow-charging device may continue to charge, e.g., to support subsequent operation of the implant during data sampling and transmission.

Other objects and features of the present invention will become apparent from consideration of the following description taken in conjunction with the accompanying drawings.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
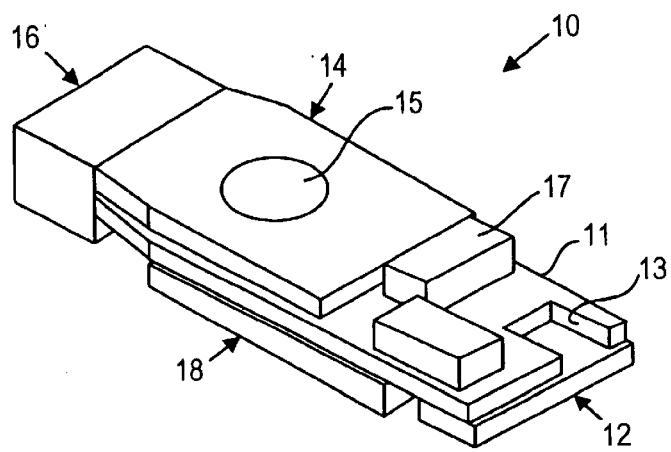
FIG. 1 is a perspective view of a preferred embodiment of a pressure sensing implant, in accordance with the present invention.
Figure 2:
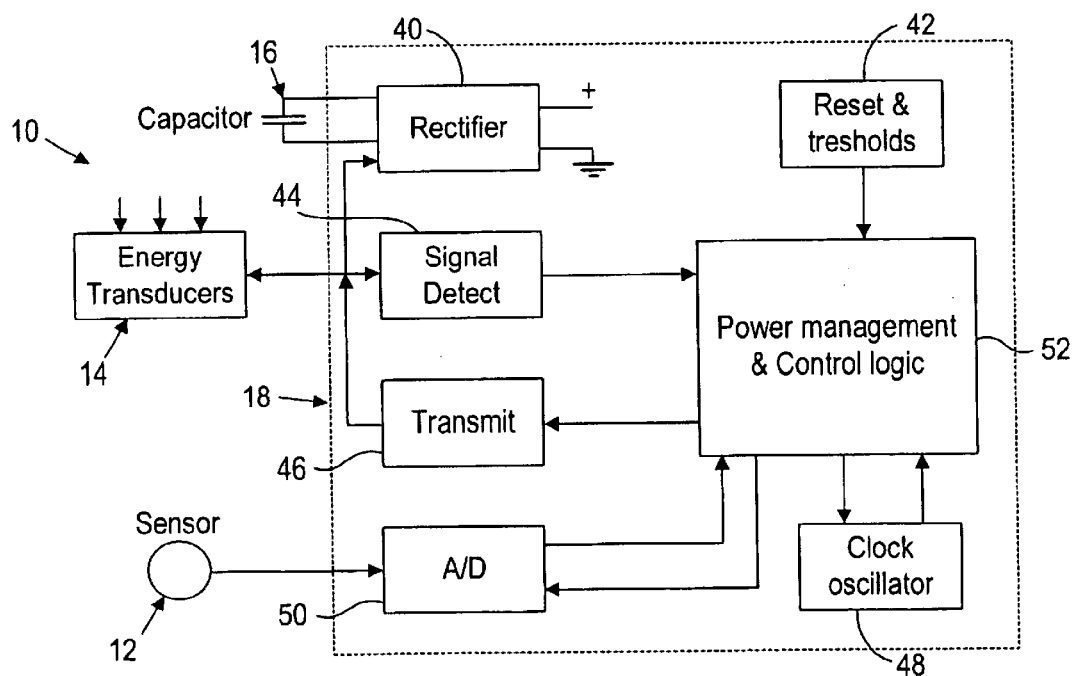
FIG. 2 is a schematic layout of the implant of FIG. 1.

Turning to the drawings, FIGS. 1 and 2 show a preferred embodiment of an implant 10, in accordance with the present invention. Generally, the implant 10 includes a sensor 12, one or more energy transducers 14, one or more energy storage devices 16, and a controller 18.

The sensor 12 is preferably a pressure sensor for measuring intra-body pressure. The sensor 12 may measure pressure within a range as low as a few millibars gauge (e.g., pressure ranges experienced within the cranium or within the pulmonary artery) and up to about 400 millibars gauge (e.g., blood pressure ranges experienced during systole). In addition, because the barometric pressure may vary by location, i.e., altitude, the absolute pressure range capacity of the sensor is preferably between about 650 and 1450 millibars absolute.

In a preferred embodiment, the sensor 12 is an absolute variable capacitance type pressure sensor. Alternatively, a piezoresistive pressure sensor may be used, although the energy consumption of this type of sensor may be substantially higher than a variable capacitance pressure sensor. For example, a typical piezoresistive sensor may have a bridge resistance of about five kiloohms (5 k$\Omega$). Assuming that one volt (1 V) is sufficient to allow pressure sampling, a current of at least about 0.2 milliAmperes (mA) would be required to operate the sensor. This may be about one hundred times more than the current required to obtain pressure samples using a variable capacitance pressure sensor.

Some reduction in power consumption of piezoresistive pressure sensors may be obtained by reducing the sampling rate of the sensor or otherwise reducing the duty cycle of the implant. Alternatively, to reduce power consumption, a sample-and-hold circuit (not shown) may be provided for capturing voltages, and an analog-to-digital converter (also not shown) may be provided for converting the voltages when desired. Thus, the current may be on for relatively short times during each sampling cycle.

Preferably, a silicon MEMS-based pressure sensor is used, because of its relative small size, e.g., smaller than about four millimeters (4 mm) maximum footprint, e.g., not more than about four millimeters (4 mm) width by four millimeters (4 mm) length. Preferably, the sensor is no larger than about 0.8 mm width by about 2.1 mm length by about 0.3 mm thickness. Silicon is a particularly useful material for the sensor 12, as it generally does not suffer from creep and fatigue, and therefore may result in a substantially stable sensor. MEMS-based sensors are presently preferred because they may be manufactured in large volume at relatively low cost compared to other sensors. Other materials that may be used include titanium, as is used for the Chronicle™ device manufactured by Medtronic, Inc. Preferably, the sensor 12 is made from biocompatible materials, although the sensor 12 may be coated, if necessary or desired, with a biocompatible and/or chemically resistive coating (not shown), as will be appreciated by those skilled in the art.

In alternative embodiments, one or more other sensors may be provided instead of or in addition to a pressure sensor. For example, the sensor 12 may include one or more biosensors capable of measuring physiological parameters, such as temperature, electrical impedance, position, strain, pH, fluid flow, and the like. U.S. Pat. Nos. 4,793,825 issued to Benjamin et al. and 5,833,603 issued to Kovacs et al. disclose exemplary embodiments of biosensors that may be provided. The disclosure of these references and others cited therein are expressly incorporated herein by reference. The sensor 12 may generate a signal proportional to a physiological parameter that may be processed and/or relayed by the controller 18 to the energy transducer 14, as described further below. Alternatively, the sensor 12 may be configured to monitor a radiation dose including ionizing, magnetic and/or acoustic radiation, to monitor flow in a bypass graft, to produce cell oxygenation and membrane electroporation, and the like.

In further alternatives, a device for providing one or more therapeutic functions (not shown) may be provided in addition to or instead of the sensor 12. For example, the device may be used to activate and/or control a therapeutic device implanted within a patient's body, such as an atrial defibrillator, a pain relief stimulator, a neuro-stimulator, a drug delivery device, and/or a light source used for photodynamic therapy.

Figure 3A:
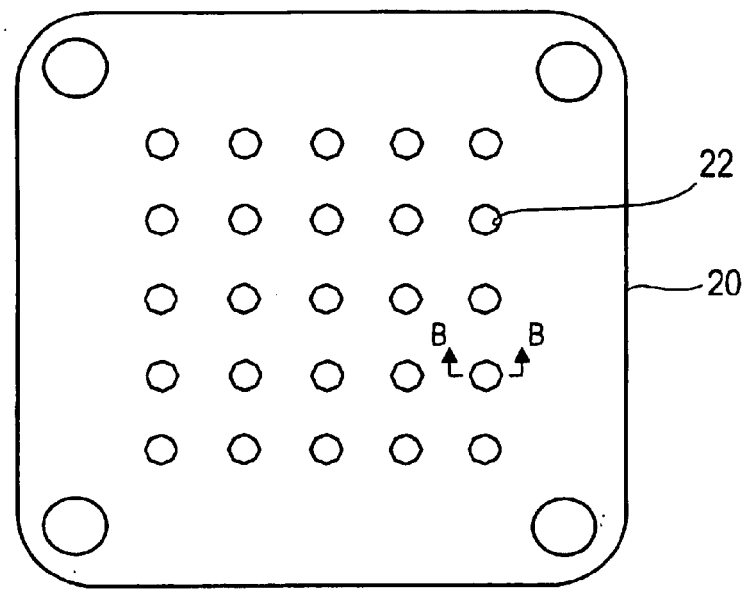
FIG. 3A is a top view of an energy exchanger that may be provided in an implant, such as that shown in FIGS. 1 and 2, in accordance with the present invention.
Figure 3B:
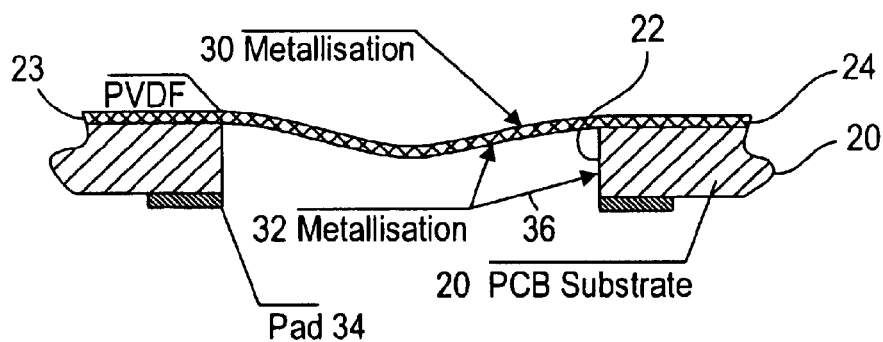
FIG. 3B is a cross-sectional view of the energy exchanger of FIG. 3A, taken along line B—B.

Turning to FIGS. 3A and 3B, the energy transducer 14 is preferably an acoustic transducer for converting energy between electrical energy and acoustic energy. As explained further below, the acoustic transducer 14 is configured for converting acoustic energy from a source external to the implant into electrical energy and/or for transmitting an acoustic signal including sensor data to a location external to the implant. In one embodiment, the energy transducer 14 is configured to operate alternatively as either an energy exchanger or an acoustic transmitter, or simultaneously as an energy exchanger and an acoustic transmitter. Alternatively, multiple energy transducers (not shown) may be provided, e.g., one or more converting acoustic energy striking the energy exchanger into electrical energy, and one or more transmitting acoustic signals to a location external to the implant 10. In a further alternative, multiple energy transducers (not shown) may be provided for increasing the electrical energy produced for a given acoustic energy transmitted to the implant 10.

The energy transducer 14 generally includes a substrate 20 including one or more cavities 22 therein, such as the array of cavities 22 shown in FIG. 3A. The cavities 22 may extend completely through the substrate 20 or only partially into the substrate 20. The cavities 22 are preferably substantially round in cross-section, although oval or other elongate slotted cavities (not shown) may be provided, which may increase sensitivity and/or efficiency as compared to a substantially round cavity. The cavities 22 may have a cross-section of about 0.5–2.5 millimeters, and preferably between about 1.0 and 1.3 millimeters (mm). For elliptical or other elongate cavities (not shown), the cavities preferably have a width of 0.2–2.5 millimeters and a length of 1.0–25 millimeters. The substrate 20 may be formed from a relatively high modulus polymer, such as poly ether ether ketone (PEEK), silicon, and/or a printed circuit board, e.g., of FR4, Rogers, a ceramic, or Kapton.

A substantially flexible piezoelectric layer 24 is attached to the substrate 20 across the cavities 22. The piezoelectric layer 24 generally includes a polymer layer 28, preferably a fluorocarbon polymer, such as poly vinylidene fluoride (PVDF). The polymer layer 28 may have a thickness of between about three and two hundred fifty micrometers (3–250 $\mu$m), and preferably about thirty micrometers (30 $\mu$m) or less. A first conductive layer 30 is provided on an external surface of the polymer membrane 28 and a second conductive layer 32 provided on an internal surface of the polymer membrane 28. The second conductive layer 32 may be coupled to a conductive region 36 provided on a wall of the cavities 22. A pad 34 is provided on a lower surface of the substrate 20 for coupling the second conductive layer 32 to a printed circuit board (not shown), as described further below.

To manufacture the energy transducer 14, a substantially flexible polymer layer 28, such as a PVDF membrane, is provided. Because PVDF is generally chemically inert, the polymer layer 28 may need to be activated, e.g., using an etching process. For example, a sodium napthalene solution may be used to chemically attack the PVDF to cleave the carbon-fluorine bonds and/or other solutions to cleave the carbon-hydrogen bonds and/or carbon-carbon bonds in the material. Alternatively, a gas phase plasma treatment, e.g., using an oxygen, air, Helium, and/or Argon plasma, may be used.

A substantially planar substrate 20 is provided, and one or more cavities 22 are formed in a surface of the substrate 20, for example, by mechanical drilling, laser drilling, or punching. Alternatively, the cavities 22 may be etched into the substrate 20, e.g., using VLSI/micro-machining technology or any other suitable technology.

A thin layer of adhesive (not shown) may be applied over the substrate 20, such as an epoxy or acrylic-based adhesive. Preferably, a relatively low viscosity (e.g., less than one thousand centi-poise) adhesive is used that may be atomized over the substrate 20. More preferably, the adhesive is light-activated, thereby facilitating positioning of the piezoelectric layer 24 over the substrate 20 before the adhesive is cured. The piezoelectric layer 24 is applied against the adhesive over the substrate 20. Alternatively, individual piezoelectric layers (not shown) may be bonded or otherwise attached over one or more individual cavities 22. The cavities 22 may be filled with a gas, such as air, to a predetermined pressure, e.g., ambient pressure or a predetermined vacuum, that may be selected to provide a desired sensitivity and ruggedness for the energy transducer 14.

The assembled substrate 20 and piezoelectric layer 24 may be placed in a pressure chamber, and a predetermined pressure applied against the piezoelectric layer 24. This may cause the piezoelectric layer 24 to press against the substrate 20, e.g., to facilitate spreading the adhesive more evenly between the substrate 20 and the piezoelectric layer 24. In addition, the predetermined pressure preferably causes the piezoelectric layer 24 to at least partially enter the cavities 22, thereby creating depressions in the piezoelectric layer 24 corresponding to the cavities 22, as best seen in FIG. 3B. Optionally, the pressure chamber may be heated to a predetermined temperature to facilitate creating the depressions and/or cure the adhesive. In addition or alternatively, the adhesive may then be cured, e.g., by exposing the assembled substrate 20 and piezoelectric layer 24 to visible or ultraviolet light, pressure, and/or heat for a predetermined time.

Thus, the piezoelectric layer 24 may include depressions, which may be useful for enhancing the efficiency and/or sensitivity of the energy transducer 12. For example, the depressions may enhance the conversion of an acoustic pressure wave striking the piezoelectric layer 24 into mechanical strain, resulting in an increased yield of electrical energy for a given pressure amplitude. The depressions may also be used to customize the natural resonant frequency of the piezoelectric layer 24. The depth of the depressions may be between about one and two hundred micrometers (1–200 $\mu$m), and preferably between about twenty and one hundred micrometers (20–100 $\mu$m), although depths greater than this may also increase efficiency as compared to a planar piezoelectric layer 24 without depressions. To ensure that these depths are consistently reproducible, the depth of the depressions may be measured, for example, using a non-contact optical profiler.

Both surfaces of the polymer layer 28 may be coated with conductive layers 30, 32, preferably metallization layers, at any stage of manufacturing. For example, the conductive layers 30, 32 may be applied either before or after the piezoelectric layer 24 has been bonded to the substrate 20. Because the current encountered during use of the energy transducer 14 is relatively low (e.g., about thirty microamperes (30 $\mu$A) or less, and preferably about five microamperes (5 $\mu$A) or less), a thickness of the conductive layers 30, 32 may be relatively thin, e.g., fifteen micrometers (15 $\mu$m) or less, and more preferably about two hundred nanometers (200 nm) or less. The thickness of the conductive layers 30, 32 may be substantially equal to or different from one another. For example, the first or outer conductive layer 30 may be substantially thicker than the second or inner conductive layer 32 to protect the energy transducer 14 from environments to which it is exposed, such as those encountered within a human body. The conductive layers 30, 32 may be formed from biocompatible and/or metallic materials, including one or more of gold, platinum, titanium, tantalum, palladium, vanadium, copper, nickel, silver, and the like.

The conductive layers 30, 32 may be coated on the surfaces of the polymer layer 28 using any known method, such as depositing an electro-less nickel, gold, or copper base layer, followed by depositing a galvanic coating, including any of the materials listed above. The conductive layers 30, 32 may be deposited using physical vapor deposition, chemical vapor deposition, sputtering, and/or other gas phase coating processes known to those skilled in the art. The conductive layers 30, 32 may be applied as single layers or as multiple layers of one or more materials in order to optimize the layers' electrical, mechanical, and/or chemical properties. Exemplary methods for making the piezoelectric layer 24 may be found in "Handbook of Physical Vapor Deposition (PVD) Processing," Donald M. Mattox (ISBN 0-8155-1422-0 Noyes publications, 1998) and "Handbook of Deposition Technologies for Films and Coatings," Rointan F. Bunshah (ed.), (Noyes Publications; ISBN: 0815513372 2nd edition 1994.) The disclosures of these references, as well as any others cited therein, are incorporated herein by reference.

The method described above may be used to make individual energy transducers or alternatively to make a plurality of energy transducers. For example, a plurality of energy transducers may be made as a single panel, and, after the metallization process, the panel may be separated into individual energy transducers. The separation may be accomplished using known dicing systems and methods, for example, using a dicing machine known to those in the microelectronics industry for dicing silicon wafers, a knife cutter, a milling machine, or a laser, e.g., a diode laser, a neodymium YAG laser, a $CO_2$ laser, or an excimer laser. Upon separation of the individual energy transducers, the electrical impedance of each of the energy transducers may be measured to confirm their integrity and proper operation. Additional information on acoustic transducers or energy exchangers appropriate for use with implants in accordance with the present invention may be found in U.S. Pat. No. 6,140,740, the disclosure of which is expressly incorporated herein by reference.

In an alternative embodiment, the substrate 20 may be formed from silicon, with or without electronics. The cavities 22 may be formed therein, the piezoelectric layer 24 may be attached to the substrate 20, and the surfaces metalized, generally as described above. In order to avoid large capacitances, an insulating oxide or other ring (not shown) may be provided around the cavities 22. The bottom of the cavities 22 may be sealed using an adhesive, e.g., an underfill adhesive used during the flip-chip process.

Returning to FIGS. 1 and 2, the energy storage device 16, preferably one or more capacitors, is coupled to the energy transducer 14. In a preferred embodiment, the capacitor may be a tantalum or ceramic capacitor, e.g., a 10.0 μF tantalum capacitor, such as model no. TACL106K006R, sold by AVX. Alternatively, the energy storage device 16 may be a battery or other known device, preferably capable of storing electrical energy substantially indefinitely. In addition, the energy storage device 16 may be capable of being charged from an external source, e.g., using acoustic energy, as described further below. In an alternative embodiment, the energy storage device 16 may include both a capacitor and a primary, non-rechargeable battery (not shown). Alternatively, the energy storage device 16 may include a secondary, rechargeable battery and/or capacitor that may be energized before activation or use of the implant 10. For example, the energy storage device 16 may include a first relatively fast-charging capacitor and a second relatively slow-charging capacitor (not shown).

Turning to FIG. 2, the controller 18 may be an Application Specific Integrated Circuit (ASIC) and/or a plurality of discrete electronic components. The controller 18 generally interfaces between the sensor 12, the energy transducer 14, and/or other active or passive components of the implant 10. The controller 18 is also coupled to the energy storage device 16 for receiving electrical energy to operate the controller 18 and/or other components of the implant 10. The controller 18 generally includes a rectifier 40, reset and threshold circuitry 42, signal detect circuitry 44, transmission circuitry 46, a clock oscillator 48, an analog-to-digital converter 50, and power management and control logic circuitry 52. In addition, the controller 18 may include a voltage reference circuit, e.g., a bandgap reference, a Zener device, or a buried Zener device.

The rectifier 40 is coupled to the energy transducer 14 for converting electrical energy generated by the energy transducer 14 into a form suitable for powering components of the implant 10. For example, the rectifier 40 may be configured for converting incoming alternating current (AC) voltage from the energy transducer 14 into direct current (DC) voltage for storage by the energy storage device 16 and/or for powering the controller 18 and other components of the implant 10. The rectification may be performed by diodes arranged in a configuration suitable for the requirements of the mode of operation, preferably resulting in a passive circuit that draws substantially no current.

Figure 4:
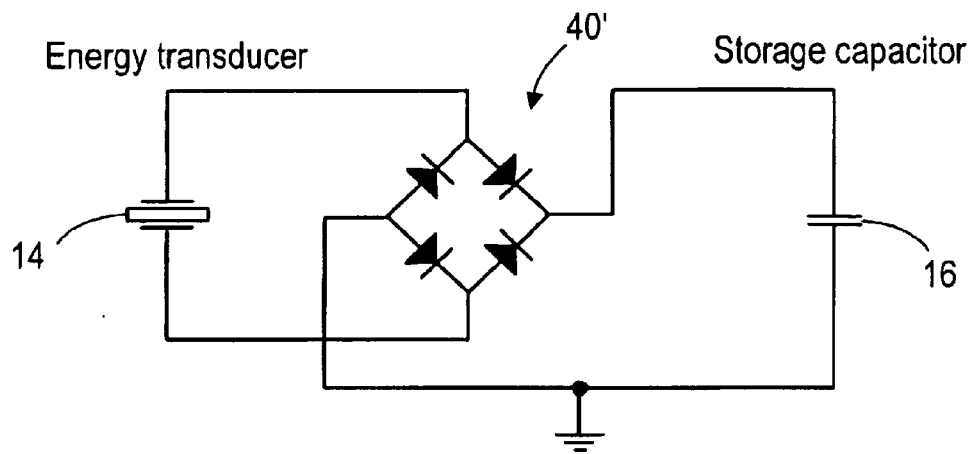
FIG. 4 is a schematic of a first preferred embodiment of a rectifier for use with an implant, such as that shown in FIG. 2.

FIG. 4 shows a first preferred embodiment of a full-bridge rectifier 40' that may be provided. The energy transducer 14 and energy storage device 16 may be connected to the rectifier 40' such that AC current generated by the energy transducer 14 is converted into DC current for charging the energy storage device 16. The full-bridge configuration of the rectifier 40' may yield relatively high current and power efficiency that may be suitable for "full-duplex" operation of the energy transducer 14, i.e., where the energy transducer 14 simultaneously converts external acoustic energy into electrical energy and transmits an acoustic signal.

Figure 5:
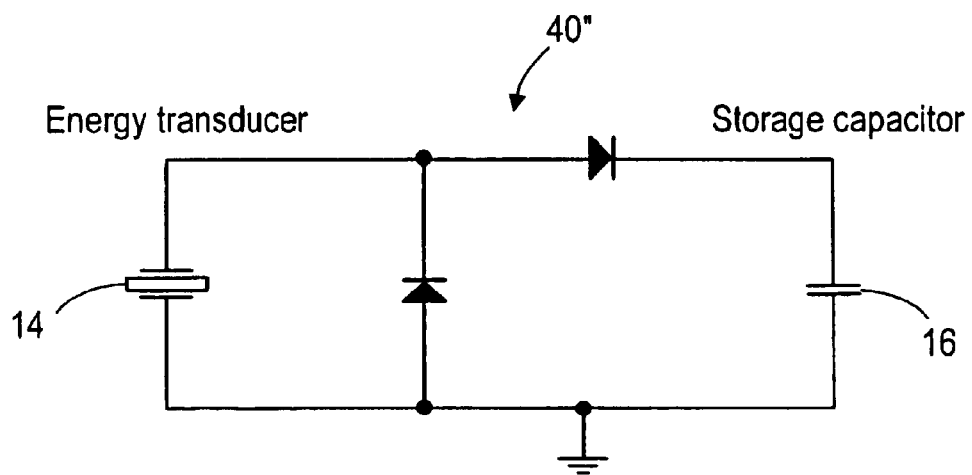
FIG. 5 is a schematic of a second preferred embodiment of a rectifier for use with an implant, such as that shown in FIG. 2.

FIG. 5 shows a second preferred embodiment of a voltage-doubler rectifier 40" that may be used. The configuration of this rectifier 40" may yield less current than the rectifier 40' shown in FIG. 4, although it may generate a relatively higher voltage for a given acoustic excitation of the energy transducer 14. This rectifier 40" may be better suited for "half-duplex" operation, i.e., where the energizing and transmitting functions of the energy transducer 14 are temporally distinct. This embodiment may also only require two diodes to operate and may keep one side of the energy transducer 14 substantially grounded, thereby simplifying construction of the implant 10.

Alternatively, other rectification circuits (not shown) may be used, including Schottky diodes, voltage triplers or other multiplier circuits, and the like. In addition, the rectifier 40 may include an overvoltage protector (not shown), which may prevent the energy storage device 16 from overcharging, e.g., to unsafe levels. For example, the overvoltage protector may include a Zener diode, or a transistor that opens at a predetermined threshold voltage.

Returning to FIG. 2, the reset and threshold circuitry 42 is coupled to the energy storage device 16 for monitoring for particular events. For example, the reset and threshold circuitry 42 may reset the controller 18 as the energy storage device 16 is recharging. This "power-on" reset function may occur when the capacitor voltage of the energy storage device 16 reaches a predetermined charging voltage, e.g. 3.8 V. In addition, during operation of the implant 10, the reset and threshold circuitry 42 may automatically turn the controller 18 and/or other components of the implant 10 off when the capacitor voltage of the energy storage device 16 drops below a predetermined shutdown voltage, e.g., 1.5 V.

The reset circuitry 42 preferably monitors the voltage of the energy storage device 18 in a substantially passive manner. For example, the reset circuitry 42 may include a field-effect transistor (FET) that is switched on when its gate voltage exceeds a predetermined threshold. Thus, the reset circuitry 42 may be passive, i.e., drawing substantially no current from the energy storage device 16.

The signal detect circuitry 44 generally is coupled to the energy transducer 16 for monitoring when the energy transducer 16 is receiving acoustic signals from a source external to the implant 10. Preferably, the signal detect circuitry 44 is a passive FET circuit, thereby drawing substantially no current. The signal detect circuitry 44 may also include a smoothing capacitor (not shown) and/or logic for reducing the sensitivity of the signal detect circuitry 44 to spurious transient signals. The signal detect circuitry 44 may provide a communication channel into the implant 10, e.g., to pass commands and/or information in the acoustic excitation signals received by the energy transducer 16 for use by the controller 18. In addition, the signal detect circuitry 44 may pass commands or other signals to controller 18, e.g., that acoustic excitation signals have been discontinued, and/or that the implant 10 should become operative. For example, when the implant 10 is configured for operation in half-duplex mode, the signal detect circuitry 44 may monitor for termination of an energizing transmission for charging the energy storage device 16, whereupon the controller 18 may begin sampling and/or transmitting sensor data.

The transmission circuitry 46 is coupled to the energy transducer 14, and is generally responsible for preparing signals for transmission from the implant 10 to a location exterior to the implant 10. The signals are preferably digital electrical signals, which may be generated, for example, by grounding one pin of the energy transducer 14 and alternately connecting the other pin between ground and a predetermined voltage. Alternatively, the signals may be generated by alternately grounding the first pin and connecting the second pin to the predetermined voltage, and then grounding the second pin and connecting the first pin to the predetermined voltage. In a further alternative, the signal may be processed or modulated, e.g., using spread spectrum, direct sequence mixing, CDMA, or other technologies, as will be appreciated by those skilled in the art.

Figure 6:
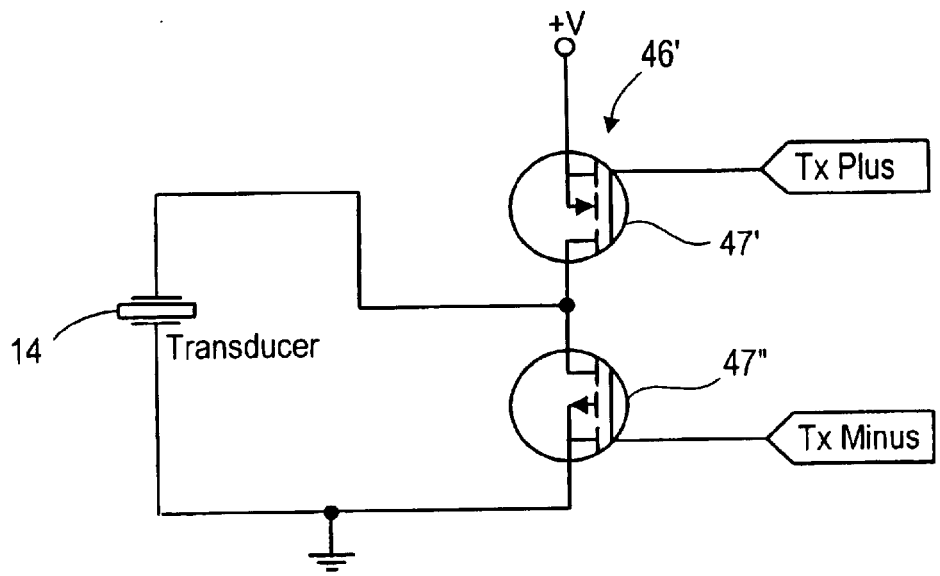
FIG. 6 is a schematic of a first preferred embodiment of a transmission circuit for use with an implant, such as that shown in FIG. 2.

FIG. 6 shows a first preferred embodiment of a transmission circuit 46' that may be used for transmitting such digital signals. The energy transducer 14 is coupled to ground and between a pair of transistors $47_1'$ and $47_2'$. The gates of the transistors $47_1'$ and $47_2'$ may be coupled to the control logic circuitry 52 (shown in FIG. 2) for receiving signals for transmission, such as sensor data signals from the sensor 12 (also shown in FIG. 2). Alternatively, the gates may be coupled directly to the analog-to-digital converter 50 (also shown in FIG. 2) or to the sensor 12. The incoming sensor data signals may alternatively couple the energy transducer 14 between ground and +V, thereby converting the sensor data signals into acoustic energy, which may be transmitted to a location exterior to the implant 10.

Figure 7:
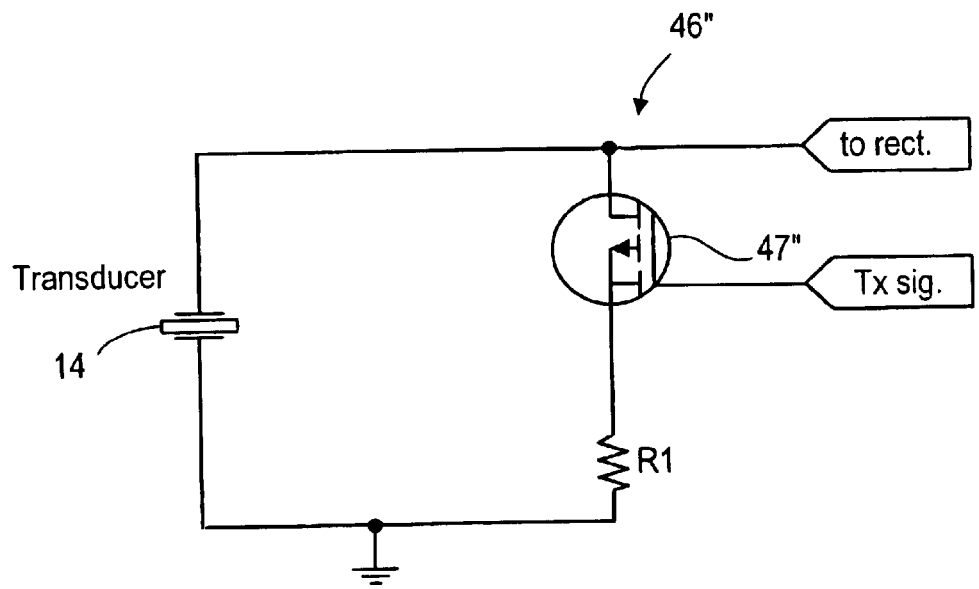
FIG. 7 is a schematic of a second preferred embodiment of a transmission circuit for use with an implant, such as that shown in FIG. 2.

FIG. 7 shows a second preferred embodiment of a transmission circuit 46" that may be provided for full-duplex operation, i.e., for simultaneously receiving an energizing signal and transmitting a data signal. For example, the energy transducer 14 may receive an energizing signal at a first frequency $f_1$, while the transmission circuit switches the transistor 49 on and off at a second frequency $f_2$, e.g., using sensor data signals. This periodic switching induces a current in the energy transducer 14 at frequencies $f_1 +/- f_2$ and possibly others. This current causes the energy transducer 14 to transmit acoustic signals at the new frequencies, which may be correlated back to the sensor data by a receiver exterior to the implant 10. In a further alternative, the transmission circuitry 46 may include analog circuitry for generating analog signals that may be transmitted by the energy transducer 14.

In an alternative embodiment (not shown), a full-bridge transmission circuit may be used for the transmission circuit. Using this circuit, pins of the energy transducer may be coupled alternately to ground and +V. For example, a first pin may be coupled to ground and a second pin coupled to +V, and then the first pin may be coupled to +V and the second pin coupled to ground. This circuit may generate signals at about twice the amplitude of the other embodiments described above.

Returning to FIG. 2, the clock oscillator 48 may provide timing and/or clocking signals for the controller 18 and/or the various components of the implant 10. For example, the clock oscillator 48 may generate signals at fixed frequencies between about twenty and sixty kilohertz (20–60 kHz).

The analog-to-digital (A/D) converter 50 is coupled to the sensor 12, and to the control logic circuitry 52 or directly to the transmission circuit 46. The A/D converter 50 may digitize the sensor output for further processing by the controller 18 and/or for transmission by the energy transducer 14, using one of a variety of known digitization systems. For a variable capacitance pressure sensor, a switched-capacitor sigma-delta converter may be provided. Alternatively, for piezo-resistive or strain-gauge sensors, a track and hold amplifier followed by a successive approximation converter may be provided.

The A/D converter 50 may also include a calibrated voltage reference, against which measurements may be performed. Preferably, this is a bandgap reference, based upon the properties of silicon transistors. Alternatively, other reference circuits, such as Zener or buried Zener diode references, may be used.

The power management and control logic circuitry 52 may include several subsystems, such as a power management unit, a reception decoder, a transmission encoder, a state machine, and/or a diagnostic unit (not shown), which may be discrete hardware components and/or software modules. For example, an ASIC-compatible microprocessor, such as a CoolRISC processor available from Xemics, may be used for the power management and control logic circuitry 52. The power management unit may be provided for switching current on and off and/or for biasing voltages of the various components of the controller 18, particularly for any analog subcircuits, on demand. Thus, power may be supplied only to those portions or components currently in need of power, in order to conserve resources of the implant 10. The reception decoder is coupled to the signal detect circuitry 44 for decoding signals extracted by the signal detect circuitry 44 into commands to be passed to other components of the implant 10. These commands may include initialization, identification, control of system parameters, requests for sensor data or other information, and the like.

The transmission encoder is coupled to the transmission circuitry 46 and generally latches digital information supplied by the A/D converter 50 and prepares it for serial transmission by the transmission circuitry 46. The information may include an acknowledgement symbol, an identification code (e.g., a model, a serial number, or other identifier identifying the implant 10), internal status information (such as capacitor voltage), and/or measurements obtained by the sensor 12. Data may be sent using an asynchronous serial protocol, including, for example, a start bit, one or more synchronization bits, eight bits of data, a parity bit, and/or a stop bit. The data transmission rate and bit structure are preferably constructed so as to avoid data corruption due to reflections and reverberations of the acoustic signal within a body. For example, each bit of information may be made up of sixteen oscillations of the acoustic wave in order to ensure fidelity of the transmission. In addition, there may be predetermined delays between sequential transmissions, e.g., to minimize interference and/or to allow reverberations to die out.

The state machine controls the operational mode of the control logic circuitry 52. For example, it may determined the current mode (e.g., idle, decode, sample, transmit, and the like), and may contain logic for switching from one mode to another.

The diagnostic unit may include circuits used during manufacturing and/or calibration of the implant 10. This unit may not be operational after system integration, but may be awakened periodically by external command, e.g., to conduct in-vivo system diagnostics.

Turning to FIG. 1, to manufacture an implant 10, in accordance with the present invention, the various components may be assembled onto a double-sided printed circuit board (PCB) 11. The PCB 11 is preferably made from FR4 or other materials commonly used in the semiconductor industry, such as polyamide, Rogers, a ceramic, or Teflon™. The PCB 11 may have a thickness of between about ten and one thousand micrometers (10–1000 μm), and preferably about 0.25 millimeter (mm) or less. The sensor 12 and controller 18 may be flip chip bonded or wire bonded to one side of the PCB 11, e.g. using anistropic glue, a conductive adhesive, a nonconductive adhesive, or solder bumps. The active sensing area of the sensor 12 may be exposed through an opening 13 in the PCB 11, since the sensing area may be disposed on the same side as the electrical pads (not shown).

Alternatively, a single-sided PCB may be used, which may result in an implant that has a smaller thickness, but which may be longer or wider to accommodate the circuits printed thereon. A longer, thinner implant may be useful for implantation in particular locations within a patient's body, as will be appreciated by those skilled in the art. In a further alternative, a single-sided or double-sided flexible PCB may be used, e.g., having a thickness of about twenty five micrometer (25 μm). After assembly, the PCB may be folded, rolled, or otherwise arranged to minimize its volume.

To protect the sensor 12 and/or to prevent drift, the sensor 12 may be covered with a protective coating, e.g., a moisture barrier (not shown). Preferably, the sensor 12 is coated with a relatively soft material, such as silicone (e.g., NuSil MED4161). This coating may substantially minimize the stiffness or stress that may be imposed upon the sensor 12, which may otherwise affect its sensitivity and stability. Other protective and/or moisture barrier layers may then be applied over this coating, such as a relatively thin metal layer and/or Parylene C, without significantly affecting performance of the sensor 12. After the sensor 12 is assembled and coated, it may be calibrated, for example, by trimming the controller 18, e.g., by fuse blowing, and/or by soldering or otherwise bonding trim resistors 17 to the print side of the PCB 11.

The energy storage device 16, preferably a capacitor, may be attached to an edge of the PCB 11, e.g., bonded using epoxy or other adhesive. Conductive glue may be used for electrical contacts. The energy transducer 14 is attached to the print side of the PCB 111, e.g., by bonding with conductive glue. Additional mechanical fixation may be achieved, if desired, using an additional adhesive, such as an epoxy, around and/or under the energy transducer 14. Alternatively, the energy transducer 14 may be bonded using a conductive epoxy for electrical pad areas, and a structural epoxy for areas away from the pads. When the energy transducer 14 is attached to the PCB 11, the active area 15 of the energy transducer 14 is disposed away from the PCB 11 and/or otherwise exposed to transmit and/or receive acoustic energy, as described further below.

Preferably, a panel of implants are assembled, e.g., by attaching the components for multiple implants onto a single PCB. To calibrate the panel (or individual implants) following assembly, the panel may be inserted into a testing and diagnostic chamber (not shown). The chamber may be thermostatically controlled to ensure substantially constant temperature. In addition, pressure within the chamber may also be controlled within pressure ranges defined by the implants' specifications, e.g., pressure ranges to which the implants may be subjected during use. Preferably, the chamber includes a "bed of nails" or similar fixture (also not shown) that provides contact between desired electrical pads on the PCB and the conductive "nails." The nails are coupled to external diagnostic electronics that may perform diagnostics and calibration, e.g., via trimming, as required. Thus, the diagnostic electronics may communicate and/or control the implants on the panel via the nails. The testing generally includes calibration of the pressure sensors' sensitivity and offset, e.g., based upon comparison of measurements of the implants to a calibrated pressure sensor, and/or calibration of the frequency of the internal oscillator.

Once the panel has been assembled and/or calibrated, the panel may be separated into individual implants. For example, the panel may be diced using a milling machine, a dicing machine such as that used for dicing silicon wafers, a laser, or a knife-based cutter. If desired, an intermediate moisture barrier, such as Parylene C, may be applied to any or all of the components, e.g., the pressure sensor, the controller, etc., to provide additional protection for the covered components.

After separation, each implant 10 is generally placed within a box or other casing (not shown). The casing may protect the implant 10 from penetration of moisture or other body fluids, which may cause corrosion of the electrical pads or traces and/or may cause drift. The casing may also provide mechanical protection and/or may provide connection points from which to attach the implant 10, e.g., to other devices that may also be implanted within a patient. The casing may be provided from titanium, gold, platinum, tantalum, stainless steel, or other metal. Alternatively, other biocompatible materials may be used, e.g., a polymer, such as a fluorocarbon, polyamide, PEEK, preferably covered with a metallization layer to improve the polymer's performance and/or to enhance its moisture resistance. The casing may also include a connector or other attachment fixture that may facilitate connecting the implant to other devices implanted within a patient's body, e.g., for receiving a suture that extends from a stent-graft or other implanted device.

Preferably, the casing is a five-sided box, and the implant 10 is disposed within the box such that the active areas of the sensor 12 and the energy transducer 14 are exposed through the open side. The implant 10 may be sealed within the box. For example, after assembly, a lid (not shown) may be attached to the sixth side, e.g., by welding, soldering, brazing, gluing, and the like. The lid may include openings corresponding to the active areas of the sensor 12 and/or the energy transducer 14, the perimeters of which may be sealed. Alternatively, a six sided casing may be used, having one side made of a relatively thin foil, e.g., only a few microns thick. In a further alternative, a six-sided compartment may be used, with one or more walls or one or more regions of walls being thinner than the others. The interior of the casing may be filled with a non-ionic solution, e.g., silicone oil, silicone gel, or other low modulus material, for coupling the pressure sensor and the energy transducer to the foil or thin-walled regions. U.S. Pat. No. 4,407,296 issued to Anderson, the disclosure of which is expressly incorporated herein by reference, discloses a casing that may be appropriate for use with an implant, in accordance with the present invention.

With the implant 10 within the casing, it may placed in a vacuum oven, e.g., at a temperature of about eighty degrees Celsius (80 C.) for outgassing, followed by plasma treatment for surface activation. The implant 10 may be attached to the casing using an adhesive, such as an epoxy, or silicone. The outer surface of the assembled casing and implant may be covered with a layer of Parylene C for improving corrosion resistance, a polymer to improve biocompatibility, and/or a metal deposition layer to provide a final moisture barrier. Preferably, a metal coating may be applied, which may electrically ground the casing with the energy transducer 14, and then a final coating of Parylene C or other corrosion resistance coating may be applied.

Figure 8A:
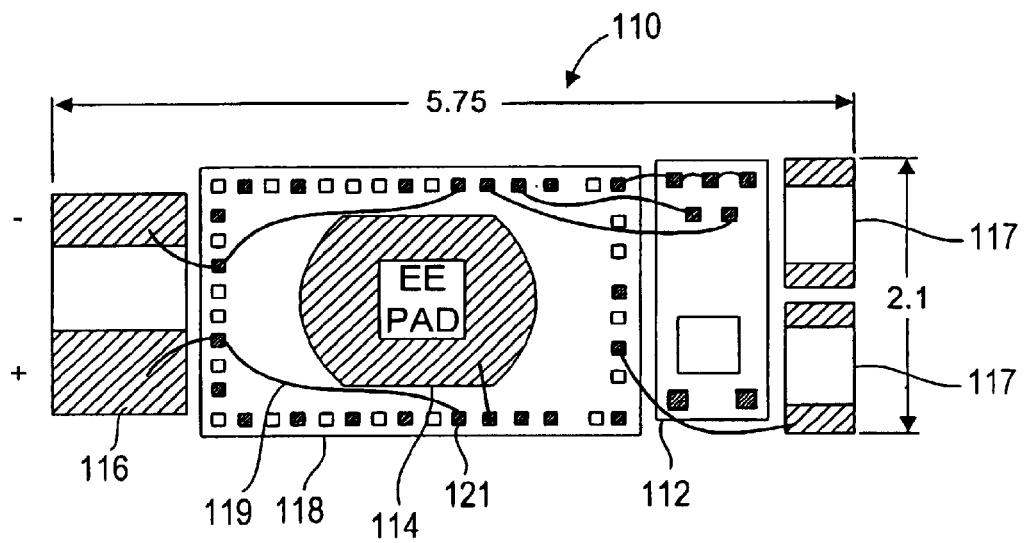
FIG. 8A is a top view of an alternative embodiment of an implant, in accordance with the present invention.
Figure 8B:
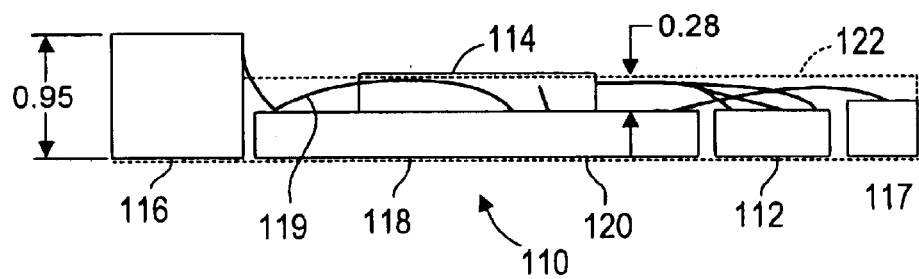
FIG. 8B is a side view of the implant of FIG. 8A.

Turning to FIGS. 8A and 8B, in an alternative embodiment, an implant 110 may be assembled using wire bonding rather than the flip-chip process described above. Similar to the previous embodiment, the implant 110 generally includes a sensor 112, one or more energy transducers 114, one or more energy storage devices 116, and a controller 118, which may include any of the subsystems or components described above. The implant 110 may be mounted within a casing (not shown), which may be formed from Titanium or other material, similar to the previous embodiment. In the exemplary embodiment shown, the overall dimensions of the implant 110 may be not more than about 5.75 mm long, 2.1 mm wide, and 0.95 mm deep. The casing may have a width about 0.1 mm wider than the widest component, e.g., the controller 118, and a depth of about 1.3 mm. Of course, these dimensions are only exemplary and may be varied to accommodate different size components or to facilitate implantation within predetermined locations within a patient's body.

During assembly, the sensor 112, the energy storage device(s) 116, and the controller 118 may be attached to the casing, e.g., to a bottom panel 120 (shown in phantom in FIG. 8B). After fabricating the energy transducer(s) 114, e.g., using the methods described above, the energy transducer(s) 114 may be attached to the controller 118, e.g., to an upper surface, as shown. The energy storage device(s) 116, e.g., one or more capacitors, may be coated, e.g., to electrically isolate the positive terminal and/or other portions of the energy storage device(s) 116.

Wires 119 may be bonded to provide any required electrical connections between the components, e.g., between the sensor 112, the energy exchanger(s) 114, the energy transducer(s) 116, and/or the controller 118. For example, the components may include one or more electrical contacts 121 to which ends of respective wires 119 may be soldered or otherwise bonded using known methods. The wires 119 may be bonded before testing the controller 118, e.g., in order to test operation of the entire implant 110. Alternatively, the wires 119 may be bonded after testing the controller 118 and/or other components individually or at intermediate stages of testing. For example, testing, calibration, and/or trimming the controller 118 may be completed using a probe card (not shown) that may be coupled to leads on the controller 118, e.g., similar to the bed of nails described above. During or after testing, trim resistor(s) 117 may be attached to the bottom 120 of the casing and/or electrically coupled to the controller 118 or other component. The trim resistor(s) 117 may be electrically isolated from the other components.

The subassembly may be cleaned and/or coated, similar to the previous embodiment. For example, the entire subassembly may be coated with Parylene or other moisture barrier. The sensor may be coated, for example, with silicone (NuSil), which may still expose an active area of the sensor, e.g., a membrane of a pressure sensor, to body conditions. Ground connections may be made, e.g., for the trim resistors 117 and/or other components. The casing may then be at least partially filled with potting compound, e.g., using a mold to protect the active area of the sensor 112. Preferably, the potting compound is filled to line 122 (shown in phantom in FIG. 8B), thereby covering all of the components, except the active area of the sensor 112 and/or the active area of the energy transducer(s) 114.

A lid, membrane, or other seal (not shown) may be attached to the casing to protect the implant 110 from an exterior of the casing, while still coupling the active areas of the sensor 112 and/or the energy transducer 114 to the exterior, similar to the previous embodiment. The space within the casing above the potting compound 122 may be filled with a fluid to acoustically couple and/or otherwise couple the active areas to the lid, membrane, or other seal. The lid may be attached first to the energy transducer 114 and then may be secured across an open end of the casing and/or the lid may be welded to the casing open end using a laser, electron beam plasma, magnetic welding, or any other welding method. The welding may be performed in a gas environment, preferably an inert gas (e.g., helium or argon), or while the parts are immersed within a fluid. Alternatively a thin membrane may be chemically etched or diffusion bonded to the lid.

Wire bonding may have advantages over the flip-chip process described above. For example, wire bonding may eliminate need for the PCB 11, and may allow the pressure sensor or other sensor to be mounted face up within the casing, which may simplify assembly. In addition, wire bonding may allow the implant 110 to be narrower in width and/or shorter in length than the previous embodiment. Because of the elimination of the PCB 11, the implant 110 may be easier, less expensive, and/or faster to assemble.

Figure 9:
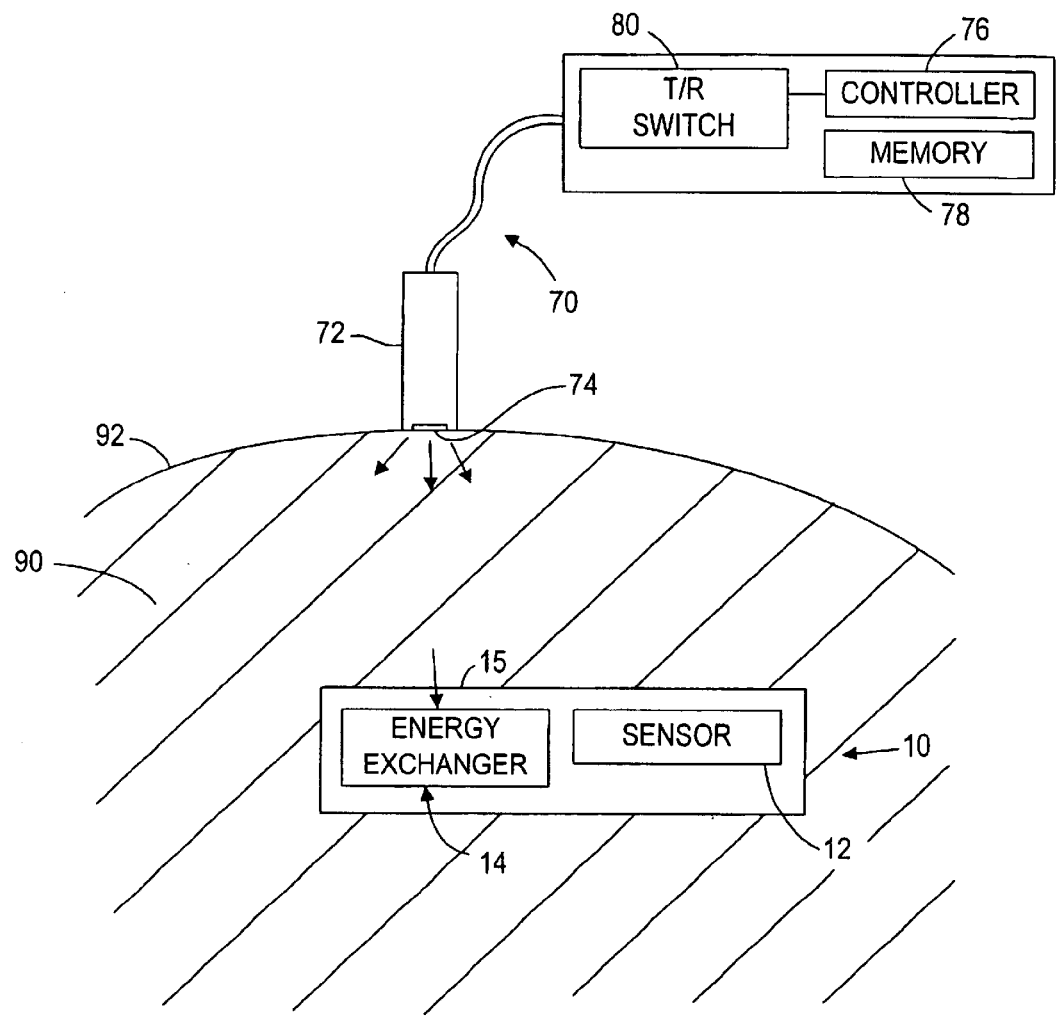
FIG. 9 is a cross-sectional view of patient's body, showing an external device communicating with an implant located within the patient's body.

Turning to FIG. 9, during operation of an implant in accordance with the present invention, such as the implant 10, e.g., upon implantation within a patient's body 90, the implant 10 may be configured to operate in a "half-duplex" mode. In this mode, an external transducer 70 located outside the patient's body 90 may be used to control, charge, and/or communicate with the implant 10. The external transducer 70 includes a probe 72 having one or more energy transducers 74, e.g., similar to the energy transducer of the implant 10, for converting energy between acoustic energy and electrical energy. The external transducer 70 also generally includes control circuitry 76, memory for storing data 78, and a transmitting/receiving (T/R) switch 80, which may be separate from, but coupled to, the probe 72, or may be within the probe (not shown). The T/R switch 80 may toggle the energy transducer 74 to operate in one of two modes, an energizing mode for charging or activating the implant 10, and a receiving mode for receiving data from the implant 10. As described below, the external transducer 70 may automatically switch between these two modes one or multiple times during use.

First, the probe 72 may be coupled to the patient, e.g., placed against the patient's skin 92, and the energy transducer 74 operated in the energizing mode, transmitting acoustic energy from its energy transducer to the implant 10 through the patient's body 90. The acoustic energy from this energizing transmission passes through the patient's body 90, at least some of the energy striking the active area 15 of the energy transducer 14 of the implant 10. The energy transducer 14 converts the acoustic energy into electrical energy, e.g., which may be used to charge the energy storage device (not shown) or otherwise operate the implant 10, and/or to receive commands from the external transducer 70, as explained further below.

Initially, the external transducer 70 may be operated in a diagnostic mode. For example, the external transducer 70 may transmit a broadband signal or a scanning signal, i.e., scanning through a range of frequencies, and wait for the implant 10 to respond. The implant 10 may transmit at different frequencies in response to the diagnostic signal, and the external transducer 70 may determine the optimal frequency for communicating with the implant based upon the responses. For example, the external transducer 70 may repeatedly charge the implant 10 using different frequency signals and measure the length of time that the implant 10 is capable of sampling and transmitting data signals at each frequency to determine the optimal frequency. Alternatively, when the implant 10 detects the signal, it may transmit a response, the response being at an optimal frequency that should be used to communicate with the implant 10.

Once the external transducer 70 has determined the optimal frequency for communicating with the implant 10 (or the external transducer 70 may already know the proper frequency to use), the external transducer 70 may then begin its operation in energizing mode, transmitting acoustic energy from its energy transducer 74 through the patient's body 90 to the implant 10, which is stored in the energy storage device. The energy storage device may continue to store energy until a predetermined voltage is achieved, e.g., about eight Volts (8 V), and then the controller (not shown) may automatically disconnect the energy storage device from the energy transducer 14. Alternatively, the energy storage device may continue to store energy until a stop command is transmitted by the external transducer 70.

After a predetermined time, e.g., between about five and sixty seconds (5–60 sec.), the external transducer 70 may automatically cease the energizing transmission. At the end of the energizing transmission, the external transducer 70 may send an identification code, e.g., a predetermined pulse sequence, identifying a specific implant. In addition, the external transducer 70 may send a stop command, an activation command, a sampling rate instruction, or one or more other instructions. The external transducer 70 may then automatically switch to receiving mode and await data transmission from the implant 10 matching the identification code. Alternatively, the external transducer 70 may be switched manually to its receiving mode.

The controller of the implant 10 may detect the end of the energizing transmission and the identification code. The controller may confirm that the identification code matches the implant 10, and automatically activate the implant 10. Alternatively, the controller may acquire an activation command or other instructions from the external transducer 70, such as a sampling rate and the like, and activate in accordance with the instructions.

For example, once activated, the implant 10 may draw electrical energy from the energy storage device, and begin to sample data using the sensor 12. The controller may receive signals, e.g., raw pressure readings, from the sensor 12, digitize and/or otherwise process the signals, and transmit sensor data using the energy transducer 14. For example, the A/D converter may convert the raw pressure readings into digital data signals, which may be further processed by the controller in preparation for data transmission. The energy transducer 14 may convert the processed digital data signals from the controller into acoustic energy that may be transmitted through the patient's body 90 to the external transducer 70.

The implant 10 may continue to sample data and transmit the data signals until the voltage of the energy storage device 16 falls below a predetermined threshold, e.g., below a level at which the pressure sensor may not continue to operate effectively, such as 1.5 volts. For example, using a 4.7 $\mu F$ tantalum capacitor for the energy storage device 16, the implant 10 may operate for between about two and six seconds (2–6 sec.). After the voltage falls below the predetermined threshold, the controller may automatically discontinue operation of the implant 10 and return to a passive state until energized and activated by the external transducer. The controller may also include additional information in the data transmission, e.g., an initial confirmation of instructions received from the external transducer, an identification code identifying the implant 10, and/or a stop notice when the signal transmission is being discontinued.

Thus, the external transducer 70 and one or more implants within the patient may operate in a cooperative manner. The external transducer 70 may energize one or more implants with an energizing transmission and/or may send instructions to individual or multiple implants. Thus, the external transducer 70 may selectively activate and receive data from one or more implants. The activated implant(s) may acquire data, transmit data signals to the external transducer 70 as acoustic energy, and then automatically return to their passive mode awaiting further instructions. The external transducer 70 may receive data from the one or more implants, which may be stored in memory 78 of the external transducer 70 or transferred to other equipment for use by medical personnel and the like.

In an alternative embodiment, the energy storage device may include a first relatively fast-charging capacitor and a second relatively slow-charging capacitor (not shown). For example, the first capacitor, which may be a relatively low-value capacitor, may be coupled to the energy transducer 14 initially, and, once the first capacitor is charged, the second capacitor, which may be a much higher value capacitor, may then be coupled to the energy transducer 14. In addition, once the first capacitor is charged, the controller may automatically transmit a signal to the external transducer, thereby opening a communication channel with the external transducer, e.g., identifying the implant 10, identifying its optimal communication frequency, and the like.

For example, the first capacitor may charge in about fifty to two hundred milliseconds (50–200 ms), thereby allowing the implant to respond promptly upon detecting a signal from an external transducer, e.g., within about fifty to two hundred milliseconds (50–200 ms). The charge retained by the first capacitor, however, may only allow the implant 10 to transmit a short reply, e.g., an identification code or other one or two word acknowledgement, in response to an interrogation from the external transducer. The second capacitor may retain a more substantial charge, e.g., that may be used to operate the implant 10 for more extended periods of time, similar to the embodiment described above.

In a further alternative embodiment, the external transducer 70 and implant 10 may operate in a quasi-continuous state, i.e., alternating between energizing/charging modes and transmitting/receiving modes. For example, the external transducer 70 may transmit an energizing transmission, e.g., for between about one and one hundred milliseconds (1–100 msec.), to charge the energy storage device with sufficient energy to operate the implant 10 for a predetermined time, e.g., several milliseconds. The external transducer 70 may then switch to receiving mode, and the implant 10 may become activated, as described above, and sample and transmit data. After the predetermined time, the implant 10 may automatically switch back to charging mode and wait for another energizing transmission from the external transducer 70. After receiving the data transmission from the implant 10, the external transducer 70 may switch back to the energizing mode and transmit another energizing transmission to recharge the implant 10. Thus, the process of "interrogating," i.e., requesting data from the implant 10, and transmitting sensor data may be repeated substantially indefinitely, as desired. For example, the external transducer 70 and implant 10 may operate at a predetermined duty cycle, e.g., at a rate of about fifteen to thirty Hertz (15–30 Hz), depending upon how much information is needed. This mode of operation may allow a smaller capacitor or other energy storage device to be used, while still allowing substantially continuous monitoring with no specific duration limit.

This quasi-continuous mode may also be implemented by the implant 10 in a hybrid mode. The external transducer 70 may transmit an energizing signal whenever the operation of the implant 10 allows it. For example, when the implant 10 is obtaining and/or processing data or between bits being transmitted by the implant 10, the energy transducer 14 may be available to receive additional energy from the external transducer. These additional energizing signals may be used to "top off" the charge on the energy storage device, thereby substantially extending the length of time that the implant 10 may operate.

In a further alternative embodiment (not shown), the implant may be operated in full-duplex mode. To facilitate this mode, the energy transducer is generally configured to transmit at a different frequency than the data signal transmissions of the implant. This may be achieved by providing one or more separate energy transmitters and receivers in the external transducer. Alternatively, the external transducer may include a single energy transducer and a circuit for separating the data transmission frequency, similar to the transmission circuit shown in FIG. 7 and described above. Thus, the external transducer and the implant may both be configured for filtering and/or otherwise separating the two transmissions from one another. Full-duplex mode may allow the implant truly to operate continuously. Because the energy transducer of the implant may receive energy substantially continuously from the external transducer via the energizing transmission, the implant may sample and transmit data substantially indefinitely, if desired, or until a stop command is transmitted from the external transducer.

Although full-duplex mode allows continuous operation of the implant, the half-duplex mode also has advantages over the full-duplex mode. First, because of its higher efficiency, i.e., only activating components as they are needed, half-duplex mode may reduce the amount of energy consumed by the implant 10, allowing the implant 10 to operate at higher voltages, although for relatively short periods of time. Second, simultaneous energizing and transmitting in full-duplex mode may cause interference between the energizing and data signal transmissions. In particular, because the energizing transmission is much stronger than the data signal transmission, the energizing transmission may create background noise for the signal transmission. In half-duplex mode, the energizing and data signal transmissions are separated in time, increasing the fidelity and detection of the signal transmission. Finally, half-duplex mode may allow a single energy transducer to be used as both an energy exchanger and as a transmitter, simplifying construction of the implant and possibly reducing the amount of acoustic energy needed.

It will be appreciated that the above descriptions are intended only to serve as examples, and that many other embodiments are possible within the spirit and the scope of the present invention.

What is claimed is:

1. A surgical implant, comprising:
    a sensor for measuring intra-body diagnostic data;
    a controller configured for generating an electrical communication signal containing the diagnostic data;
    one or more acoustic transducers;
    circuitry for collectively configuring the one or more acoustic transducers to convert acoustic energy received from a location external to the implant into electrical energy used to support operation of the implant, and convert the electrical communication signal received by the controller into an acoustical communication signal for transmission to a location external to the implant; and
    an energy storage device configured for storing the electrical energy converted by the one or more transducers, wherein the energy storage device comprises a first relatively fast-charging capacitor and a second relatively slow-charging capacitor, the first and second capacitors being coupled to the one or more acoustic transducers such that the first capacitor is charged first and the second capacitor is charged only upon substantially charging of the first capacitor.

2. The implant of claim 1, wherein the one or more acoustic transducers are configured by the circuitry in a full-duplex mode, such that the one or more acoustic transducers can simultaneously convert the acoustic energy into electrical energy and convert the electrical communication signal into the acoustical comunication signal.

3. The implant of claim 2, wherein the one or more transducers comprise at least one receive only transducer for converting the acoustic energy into electrical energy, and at least one transmit only transducer for converting the electrical communication signal into the acoustical communication signal.

4. The implant of claim 2, wherein the one or more transducers comprises at least one transducer, each of which is configured by the circuitry for converting the acoustic energy into electrical energy and for converting the electrical communication signal into the acoustic communication signal.

5. The implant of claim 1, wherein the one or more acoustic transducers are configured by the circuitry in a half-duplex mode, such that the one or more acoustic transducers can alternately convert the acoustic energy into electrical energy and convert the electrical communication signal into the acoustic communication signal.

6. The implant of claim 1, wherein the one or more transducers are collectively configured by the circuitry for converting an acoustic communication signal transmitted from a location external to the implant to another electrical communication signal, the controller configured for detecting the other electrical communication signal.

7. The implant of claim 6, wherein the controller is configured for extracting one or more commands from the other electrical communication signal and controlling the implant in response to the one or more commands.

8. The implant of claim 7, wherein the controller is configured for activating or deactivating the energy storage device in response to the one or more commands.

9. The implant of claim 7, wherein the controller is configured for monitoring when the one or more acoustic transducers stop converting electrical energy, and for activating the implant when electrical energy is no longer being converted by the one or more acoustic transducers.

10. The implant of claim 1, wherein the one or more acoustic transducers comprise:
    a substrate comprising a cavity; and
    a substantially flexible piezoelectric layer attached to the substrate across the cavity.

11. The implant of claim 10, further comprising a first electrode attached to an external surface of the piezoelectric layer and a second electrode attached to an internal surface of the piezoelectric layer.

12. The implant of claim 10, wherein the substrate comprises an array of cavities, and wherein the piezoelectric layer is bonded to the substrate over the cavities.

13. The implant of claim 10, wherein the piezoelectric layer comprises poly vinylidene fluoride.

14. The implant of claim 1, wherein the energy storage device is rechargeable.

15. The implant of claim 1, wherein the diagnostic data is pressure data.

16. The implant of claim 1, wherein the electrical energy is alternating current electrical energy, and wherein the controller is configured for converting alternating current electrical energy into direct current electrical energy for storage in the energy storage device.

17. The implant of claim 1, wherein the controller is configured to reset the implant when the energy storage device is being charged by the electrical energy.

18. The implant of claim 1, wherein the controller is configured for automatically switching the implant off when the electrical energy available from the energy storage device falls below a predetermined threshold.

19. A surgical implant, comprising:
a controller configured for controlling the operation of the implant and for generating an electrical communication signal;
one or more acoustic transducers;
circuitry for collectively configuring the one or more acoustic transducers to convert the electrical communication signal into an acoustical communication signal for transmission to a location external to the implant, and to convert acoustic energy received from a location external to the implant into electrical energy used to support operation of the implant; and
an energy storage device configured for storing the electrical energy, wherein the energy storage device comprises a first relatively fast-charging capacitor and a second relatively slow-charging capacitor, the first and second capacitors being coupled to the one or more acoustic transducers such that the first capacitor is charged first and the second capacitor is charged only upon substantially charging of the first capacitor.

20. The implant of claim 19, wherein the one or more acoustic transducers are configured by the circuitry in a full-duplex mode, such that the one or more acoustic transducers can simultaneously convert the acoustic energy into electrical energy and convert the electrical communication signal into the acoustical comunication signal.

21. The implant of claim 20, wherein the one or more transducers comprise at least one receive only transducer for converting the acoustic energy into electrical energy, and at least one transmit only transducer for converting the electrical communication signal into the acoustical communication signal.

22. The implant of claim 20, wherein the one or more transducers comprises at least one transducer, each of which is configured by the circuitry for converting the acoustic energy into electrical energy and for converting the electrical communication signal into the acoustic communication signal.

23. The implant of claim 19, wherein the one or more acoustic transducers are configured by the circuitry in a half-duplex mode, such that the one or more acoustic transducers can alternately convert the acoustic energy into electrical energy and convert the electrical communication signal into the acoustic communication signal.

24. The implant of claim 19, wherein the one or more transducers are collectively configured by the circuitry for converting an acoustic communication signal transmitted from a location external to the implant to another electrical communication signal, the controller configured for detecting the other electrical communication signal.

25. The implant of claim 24, wherein the controller is configured for extracting one or more commands from the other electrical communication signal and controlling the implant in response to the one or more commands.

26. The implant of claim 25, wherein the controller is configured for activating or deactivating the energy storage device in response to the one or more commands.

27. The implant of claim 25, wherein the controller is configured for monitoring when the one or more acoustic transducers stop converting electrical energy, and for activating the implant when electrical energy is no longer being converted by the one or more acoustic transducers.

28. The implant of claim 19, wherein the one or more acoustic transducers comprise:
a substrate comprising a cavity; and
a substantially flexible piezoelectric layer attached to the substrate across the cavity.

29. The implant of claim 28, further comprising a first electrode attached to an external surface of the piezoelectric layer and a second electrode attached to an internal surface of the piezoelectric layer.

30. The implant of claim 28, wherein the substrate comprises an array of cavities, and wherein the piezoelectric layer is bonded to the substrate over the cavities.

31. The implant of claim 28, wherein the piezoelectric layer comprises poly vinylidene fluoride.

32. The implant of claim 19, wherein the energy storage device is rechargeable.

33. The implant of claim 19, further comprising a sensor for acquiring diagnostic data, wherein the electrical communication signal generated by the transmission circuit contains the diagnostic data.

34. The implant of claim 19, wherein the electrical energy is alternating current electrical energy, and wherein the controller is configured for converting alternating current electrical energy into direct current electrical energy for storage in the energy storage device.

35. The implant of claim 19, wherein the controller is configured to reset the implant when the energy storage device is being charged by the electrical energy.

36. The implant of claim 19, wherein the controller is configured for automatically switching the implant off when the electrical energy available from the energy storage device falls below a predetermined threshold.

\* \* \* \* \*